United States Patent [19]

Bowers et al.

[11] Patent Number: 4,891,050
[45] Date of Patent: Jan. 2, 1990

[54] GASOLINE ADDITIVES AND GASOLINE CONTAINING SOLUBLE PLATINUM GROUP METAL COMPOUNDS AND USE IN INTERNAL COMBUSTION ENGINES

[75] Inventors: Wayne E. Bowers, Clearwater, Fla.; Barry N. Sprague, West Haven, Conn.

[73] Assignee: Fuel Tech, Inc., Stamford, Conn.

[21] Appl. No.: 897,869

[22] Filed: Aug. 19, 1986

Related U.S. Application Data

[63] Continuation-in-part of Ser. No. 796,428, Nov. 8, 1985, abandoned, which is a continuation-in-part of Ser. No. 677,954, Dec. 4, 1984, abandoned, and Ser. No. 790,738, Oct. 24, 1985, abandoned.

[51] Int. Cl.$^4$ ................................................ C10L 1/30
[52] U.S. Cl. .......................................... 44/67; 44/56; 44/68
[58] Field of Search ............................... 44/56, 67, 68; 260/429 R; 556/136

[56] References Cited

U.S. PATENT DOCUMENTS 2,875,223  2/1959  Pedersen et al. ................. 44/68
4,207,078  6/1980  Sweeney et al. ................. 44/68

OTHER PUBLICATIONS

Belluco, Organometallic & Coord. Chem. of Platinum, Academic Press, N.Y., pp. 221, 222, 226, 232, 295 to 297, 441, 442, 449, 454 & 455 (1974).
Deganello, Transition Metal Complexes of Cyclic Polyolefins, Academic Press, N.Y., pp. 97–100, 102, 227, 278, 281 to 283, 288, 289–291 (1979).
Dickson, Organometallic Chemistry of Rhodium & Iridium, Academic Press, N.Y., pp. 167–169, 178–188, 198–200, 220–226, 248, 258–260, 264, 271 & 277, 1983.
Maitlis, The Organic Chemistry of Palladium, Academic Press, N.Y., pp. 68, 70, 76, 77, 83, 93, 102, 103, 136, 158, 165, 202–204, 228, 242, 249, 254–258 (1971).
Chemical Abstracts 76 112565p (1972); 76113355g (1972).
Chemical Abstracts 82 4403z (1975).
Chemical Abstracts 97 110175w (1982) and 97 110181v (1982).

Primary Examiner—William R. Dixon, Jr.
Assistant Examiner—Margaret B. Medley
Attorney, Agent, or Firm—St. Onge Steward Johnston and Reens

[57] ABSTRACT

The invention provides gasoline additive compositions comprising solutions of at least one fuel-soluble platinum group metal compound in a solvent miscible in the gasoline, the platinum group metal complex being present in an amount sufficient to supply from 0.01 to 1.0 parts per million of the platinum group metal when added to a predetermined amount of gasoline.

Preferred solvents are oxygenated hydrocarbons such as ethanol, tetrahydrofuran, and methyl tertiary butyl ether, and will preferably be employed in amounts of less than 5% of the weight of the gasoline to provide oxygen and the metal at a weight ratio of from 1,000:1 to 100,000:1. Especially preferred compounds are those of the formula:

$$X M^{II} R_2$$

wherein X is a cyclooctadienyl ligand; M is a platinum group metal; and R is benzyl, phenyl or nitrobenzyl.

The additive compositions and fuel treated therewith improve operating efficiency of internal combustion engines in terms of increased power output per unit of fuel burned and reduce the emissions of particulates and noxious gases such as carbon monoxide and nitrogen monoxide. The additives provide beneficial results upon immediate use and over long periods of continuous use.

18 Claims, No Drawings

GASOLINE ADDITIVES AND GASOLINE CONTAINING SOLUBLE PLATINUM GROUP METAL COMPOUNDS AND USE IN INTERNAL COMBUSTION ENGINES

RELATED APPLICATIONS

This application is a continuation-in-part of commonly assigned co-pending patent application Ser. No. 796,428 filed Nov. 8, 1985, now abandoned which in turn is a continuation-in-part of prior applications Ser. No. 677,954, now abandoned filed on Dec. 4, 1984, and Ser. No. 790,738, filed on Oct. 24, 1985, now abandoned all by Bowers and Sprague, the inventors herein.

TECHNICAL FIELD

The present invention relates to improving the performance of internal combustion gasoline engines, and, more particularly, to the formulation and use of gasoline additives and fuels which burn more efficiently and with reduced noxious emissions.

Background Art

Prior investigations involving the use of platinum group metals in internal combustion gasoline engines have led to the development of the catalytic converter for emissions reduction. Reliance upon costly mechanical equipment, while less than ideal or desirable, has become standard despite the efforts of the prior art to accomplish the same result through less costly combustion improvements in terms of better combustion conditions through engine design and fuel additives. The efforts in engine design have provided significant improvements, but the twin objectives of improved operating efficiency and reduced noxious emissions are difficult to achieve simultaneously.

Experience to date with gasoline additives has been less successful. Lyons and McKone, for example, disclose in U.S. Pat. Nos. 2,086,775 and 2,151,432, adding from 0.001 to 0.085% (i.e., from 10 to 850 parts per million) of an organometallic compound or mixture to a base fuel such as gasoline, benzene, fuel oil, kerosene, or blends to improve various aspects of engine performance. Among the metals disclosed in U.S. Pat. No. 2,086,775 are cobalt, nickel, manganese, iron, copper, uranium, molybdenum, vanadium, zirconium, beryllium, platinum, palladium, chromium, aluminum, thorium and the rare earth metals, such as cerium. Among those disclosed in U.S. Pat. No. 2,151,432 are selenium, antimony, arsenic, bismuth, cadmium, tellurium, thallium, tin, barium, boron, cesium, didymium, lanthanum, potassium, sodium, tantalum, titanium, tungsten and zinc. In both disclosures, the preferred organometallic compounds were beta diketone derivatives and their homologues, such as the metal acetylacetonates, propionylacetonates, formylacetonates, and the like. While such compounds typically provide oxygen-to-metal ratios in the range of 1:1 to 1:10, no essential feature linked to the presence of oxygen is disclosed.

The Lyons and McKone disclosures state that concentrations of from 0.001 to 0.04% (i.e., from 10 to 400 parts per million) are not effective to improve combustion efficiency as introduced, but may become so upon prolonged use as catalytically active deposits are built up in the combustion chamber. The disclosure further states that about 0.01% (i.e., 100 ppm) of the organometallic compound is usually sufficient, once the requisite amount of catalytically active deposits has been built up, to perpetuate that amount of deposits by replacement of losses therefrom. The compounds disclosed were, therefore, not capable of generating any instantaneous catalytic effect at low concentrations, and to higher concentrations would provide no economic benefit. U.S. Pat. No. 2,460,780 to Lyons and Dempsey, which relates principally to water-soluble catalysts, confirms this at column 1, lines 11–36. Further, no indication was made for preferred oxidation states for the metals disclosed.

Neither of the Lyons and McKone patents disclose the use of oxygenated solvents or point to the importance of high oxygen-to-metal ratios. In Demonstration 15 in U.S. Pat. No. 2,086,775, palladium acetylacetonate was added to a fuel (not specifically identified, but presumably the leaded 65 octane gasoline employed in Demonstration 1) at a level of 0.002% (20 ppm). The weight ratio of oxygen to palladium was not mentioned, although by calculation it is found to be about 1 to 3, and the level of palladium is found to be about 10 ppm. No improvement in combustion was noted until after substantial driving.

The above-noted U.S. Pat. No. 2,460,780 to Lyons and Dempsey relates principally to employing catalysts which are soluble in water or other "internal liquid coolants" such as alcohol, water-soluble glycols or aqueous solutions of these. While catalyst levels based on the weight of metal compounds as low as 0.001% are disclosed, it is stated that for immediate catalytic effect the catalyst compounds for useful effect may be present at a level of at least 1% of the weight of the operating fuel charge. In some Examples, fuel-soluble cobalt, cerium and chromium catalysts are added to the fuel at total catalyst levels of 0.01%. No disclosure is given of fuel-soluble catalysts at levels below 0.01% or with oxygenated solvents. Moreover, where alcohol and glycols are employed with water-soluble catalysts, they are disclosed principally as solubilizing carriers for the catalysts and for their known internal cooling function at high load.

U.S. Pat. No. 4,295,816, Robinson discloses an elaborate delivery system for introducing water-soluble platinum group metal salts through the air intake of internal combustion engines to deliver platinum group metal catalysts to the combustion chamber at a level no greater than 9 mg catalyst per kilogram of fuel. The equipment is, unfortunately, more complicated than would be desired for gasoline automotive operators and the water-soluble salts employed, e.g., holids, have disadvantages alone or when dissolved.

In German Offenlegungsschrift No. 2,500,683, Brantl discloses that a wide variety of catalytic metals may be added to hydrocarbon fuels to reduce nitrogen monoxide and oxidize carbon monoxide at the moment of combustion in internal combustion engines. The disclosure states that organometallic or Grignard compounds of the metals lithium, sodium, lead, beryllium, magnesium, aluminum, gallium, zinc, cadmium, tellurium, selenium, silicon, boron, germanium, antimony and/or tin can be added to the fuel individually or as a mixture. Similarly, the metal complexes of the metals scandium, titanium, vanadium, chromium, manganese, iron, cobalt, nickel, copper, zinc, ruthenium, rhodium, palladium, osmium, iridium, platinum, silver, gold, gallium, molybdenum, lead and mercury, with different ligands, can be added to the fuel individually or as a mixture. For the platinum group metals osmium, iridium, and platinum, broad concentrations of from 0.347 to 3.123 grams per liter of fuel are suggested for the various compositions listed in the disclosure, with the range for particularly favorable results being from 0.868 to 1.735 grams per liter of fuel. Considering the cost of these metals and the compositions containing them, there is a negative incentive for employing them at the high levels stated by the disclosure to be effective. Moreover, the tetramethyl platinum compound is not known to exist.

In U.S. Pat. No. 2,402,427, Miller and Lieber disclose the use of certain diesel-fuel-soluble organic or organometallic compounds as ignition promoters at concentrations of from 0.02 to 3% (i.e., 200 to 30,000 parts per million). No platinum group metal compounds are identified and no indication is given that the disclosed compounds at the disclosed or lower levels would improve combustion in a gasoline internal combustion engine.

Other work done, in which cylinders of a diesel engine were coated with platinum metal, showed reductions in noxious emissions, but the coating wore off in a number of hours.

DISCLOSURE OF INVENTION

The present invention comprises the application of certain platinum group metal compounds which are directly soluble in gasoline-based fuels, or solvents for use in gasoline engines. The compounds, preferably in combination with a solvent for them which is also miscible in the gasoline, are employed at very small, but catalytically effective levels to provide from about 0.01 to about 1.0 parts of platinum group metal per one million parts of gasoline (ppm). For the purposes of this description, all part per million figures are on a weight to volume basis, i.e., mg/liter, and percentages are given by weight, unless otherwise indicated.

According to one its aspects, the invention provides gasoline additive compositions comprising a solution of a fuel-soluble platinum group metal compound in a solvent miscible in the fuel, the platinum group metal compound being present in an amount sufficient to supply from 0.01 to 1.0 parts per million of the platinum group metal when added to a predetermined amount of fuel.

Preferred solvents are oxygenated hydrocarbons such as ethanol, tetrahydrofuran, and methyl tertiary butyl ether, and will preferably be employed in amounts of less than 5% of the weight of the fuel. The oxygenated solvents will preferably be employed in amounts sufficient to supply oxygen at a weight ratio to the platinum group metal of at least 1000:1.

Among the preferred platinum group metal compounds are platinum group metal coordination compounds comprising a platinum group metal having a +2 or +4 oxidation state with at least one coordination site in the compound being occupied by a functional group containing at least one unsaturated carbon-to-carbon bond with an olefinic, acetylenic or aromatic pi bond configuration. Especially preferred compounds are those of the formula:

$$X M^{II} R_2$$

wherein X is a cyclooctadienyl ligand; M is a platinum group metal; and R is benzyl, phenyl or nitrobenzyl.

According to another aspect of the invention, gasoline fuel compositions of improved properties are provided, which comprise gasoline and an additive composition dissolved therein, said additive composition comprising a fuel-soluble platinum group metal compound in an amount effective to supply from 0.01 to 1.0 parts of the platinum group metal per million parts of fuel.

According to a further aspect of the present invention, there is provided a method of increasing the utilizable energy of gasoline for powering internal combustion engines, comprising admixing with said gasoline an additive composition comprising a fuel-soluble platinum group metal compound in an amount effective to supply from 0.01 to 1.0 parts of the platinum group metal per million parts of fuel.

The additive compositions according to the invention improve operating efficiency of gasoline and diesel internal combustion engines in terms of increased power output per unit of gasoline burned and reduce the emissions of particulates and noxious gases such as carbon monoxide and nitrogen monoxide. The additives provide beneficial results upon immediate use and over long periods of continuous use.

For the purposes of this description, gasoline is defined as a mixture of volatile hydrocarbons for use in a spark-ignited internal combustion engine and having an octane rating [(Research+Motor)/2] of at least 80, typically about 87 to 89 or above, and according to the more preferred aspects of the invention as having less than 1.4 grams per gallon of lead. Most preferably, the gasoline will be "unleaded" and contain no more than 0.05 grams of lead per gallon and no more than 0.1% of sulfur. Gasoline typically has a BTU value of about 19,700 calories per pound.

The gasoline additive compositions of this invention achieve the most reproducible effect in engines operated under lean conditions namely an air/fuel ratio of about 14.7:1 or leaner, so that oxygen is available. Compression ratios in the range of 7:1 to 12:1 are preferred. The additive is believed to improve combustion efficiency by speeding up flame initiation from the spark and increasing subsequent flame speed. It is well known that each cycle in a spark ignition engine varies around a mean optimum pressure pattern with maximum pressure occurring shortly after top-dead-center. This invention is believed to reduce the so-called "cyclic variation" from this optimum and thus increases the power for the same amount of fuel, which improves fuel consumption. This theory is provided to help explain the unexpected results achieved but is not meant to be limiting in any regard.

As indicated above, the preferred platinum group metal compounds are coordination compounds. These compounds, especially those coordinated with certain high molecular weight (preferably above 100 daltons) olefinic functional groups, are stable in the presence of moisture. This is extremely important due to the amounts of water present in gasoline which, for example, can typically contain dissolved water in amounts on the order of 30 ppm and frequently contains higher levels of dispersed and bulk water.

Few, if any, platinum group metal coordination compounds which are directly soluble in gasoline are available commercially. Compounds which are available often contain objectionable functional groups containing halogen and phosphorus and, therefore, are less than preferred for many internal combustion applications. Preferably, the compounds according to the present invention will have no phosphorus or have low levels which are free of significant disadvantages. We have discovered that certain platinum group metal compounds can be prepared which are soluble and stable in gasoline based fuels and actively catalyze the combustion of gasoline in internal combustion engines and reduce noxious emissions when introduced as an integral part of the fuel.

The preferred class of materials used include platinum group metal oxidation states II and IV. Compounds in the lower (II) state of oxidation are preferred due to their function in generating the catalytic effect. A significant feature of the invention is the use of platinum group metal II coordination compounds having at least one coordination site occupied by a functional group containing an unsaturated carbon-to-carbon bond of the olefinic, acetylenic or aromatic pi bond configuration. Preferably, two or more of the coordination sites will be occupied by such functional groups since the stability and solubility in gasoline and diesel fuel of compounds having such multiple functional groups are improved. While not wishing to be bound to any particular theory, it is believed that such preferred compounds in the lowest possible oxidation state are the most beneficial for producing instantaneous catalytic effect.

Occupation of one or more coordination sites with the following unsaturated functional groups has been found useful:

1. Benzene and analogous aromatic compounds such as anthracene and naphthalene.
2. Cyclic dienes and homologues such as cyclooctadiene, methyl cyclopentadiene, and cyclohexadiene.
3. Olefins such as nonene, dodecene, and polyisobutenes.
4. Acetylenes such as nonyne and dodecyne.

These unsaturated functional groups, in turn, can be substituted with nonhalogen-substituents such as alkyl, carboxyl, amino, nitro, hydroxyl and alkoxyl groups. Other coordination sites can be directly occupied by such groups.

The general formula for the preferred coordination II compounds is:

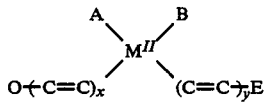

where $M^{II}$ represents the platinum group metal, with a valence of +2, where A, B, D, and E are groups such as alkoxy, carboxyl, etc. described above, where $(C=C)_x$ and $(C=C)_y$ represent unsaturated functional groups coordinated with the platinum group metal, and where x and y are any integer, typically 1 to 5.

Platinum group metals include platinum, palladium, rhodium, ruthenium, osmium, and iridium. Compounds including platinum, palladium and rhodium, especially platinum in combination with palladium and/or rhodium, are preferred in the practice of this invention.

Fuel additives containing platinum coordination compounds containing platinum in an amount of at least 10% of the total weight of all platinum group metals are preferred. Particularly good results have been achieved with additives containing a platinum coordination compound in combination with a palladium compound or palladium and rhodium compounds. Preferred weight ratios of platinum to palladium to rhodium are within the range of from 1:1:1 to 1:10:0.5.

The most preferred platinum group coordination compounds are those represented by the following formula:

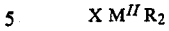

wherein X is a cyclooctadienyl ligand; M is a platinum group metal; and R is benzyl, phenyl or nitrobenzyl.

Among other suitable platinum group metal compounds, especially palladium compounds, are the following which include at least one sigma or pi carbon to platinum group metal bond.

(a) 2,2'-bis(N,N-dialkylamino)1,1'-diphenyl metals, as represented by the formula

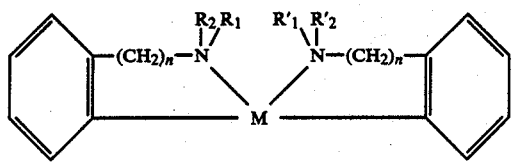

Wherein M is a platinum group metal; $R_1$ and $R_2$ are lower alkyl, e.g., from 1 to 10 carbons; and n is an integer from 1 to 5. Representative of this group is 2,2'-bis (N,N-dimethylamino)1,1'-diphenyl palladium.

(b) tetrakis (alkoxy carbonyl) metal cycloalkenes, as represented by the formula

wherein M is a platinum group metal; $R_1$ is a lower alkyl, e.g., from 1 to 5 carbons; and $R_2$ is a cycloalkene having, e.g., from 5 to 8 carbons and from 2 to 4 unsaturations within the ring structure. Representative of this group is tetrakis (methoxy carbonyl) palladia cyclopentadiene.

(c) μ-diphenyl acetylene bis ($\eta^5$-pentaphenyl cyclopentadiene) di metals as represented by the formula

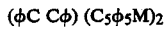

wherein M is a platinum group metal and φ is phenyl. Representative of this group is μ-diphenyl acetylene bis ($\eta^5$-pentaphenyl cyclopentadiene) dipalladium.

(d) dialkyl dipyridyl metals of the formula

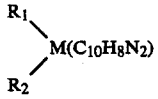

wherein M is a platinum group metal; and $R_1$ and $R_2$ are lower alkyl, e.g., having from 1 to 5 carbons. Representative of this group is diethyl dipyridyl palladium.

(e) bis (π-allyl) metals of the formula

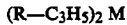

wherein M is a platinum group metal and R is hydrogen, aryl or alkyl, e.g., one to ten carbons. Representative of this group is bis (phenyl allyl) palladium.

The platinum group metal compound will be added to gasoline in an amount effective to improve engine performance in terms of operating efficiency or emissions reduction. Typically, the compound will supply an amount of the metal within the range of from 0.01 to 1.0 parts of the platinum group metal per one million parts of gasoline (ppm w/v). A more preferred range is from 0.05 to 0.5 ppm, and most preferably, the platinum group metal will be supplied at a level of from 0.10 to 0.30 ppm on this same basis.

The fuel additive composition will preferably include a solvent which is miscible in gasoline. Certain of the solvents provide enhancements in the effectiveness of the platinum group metal compound and are preferred for this reason. Among the preferred solvents are oxygenated hydrocarbons, such as alcohols, heterocyclic oxygen compounds and ethers. Particularly preferred compounds are: 1 to 4 carbon alcohols, especially ethanol; tetrahydrofuran; and methyl tertiary butyl ether. Some of these compounds, as will be seen from the examples which follow, show especially strong enhancements with particular platinum group metal coordination compounds.

The solvent will preferably be employed at a concentration of up to 5% of the fuel and typically greater than 0.25%. Solvent concentrations of from 0.25 to 2.5% are preferred, and are most preferably 1.0% or less, and in some cases show surprising improvements in additive performance when employed at these levels.

Where the platinum group metal compound, or one of the several such to be employed, is sensitive to moisture, e.g., metal acetylacetonates, it is important to maintain the moisture content of the solvent an total additive composition sufficiently low that no significant platinum group metal is precipitated. Preferably, additive compositions containing moisture-sensitive components will be substantially free from water.

The preferred fuel additives will employ sufficient amounts of platinum group metal compounds and oxygenated solvent to provide a weight ratio of oxygen to platinum group metal of from 1,000:1 to 100,000:1, preferably greater than 3,500:1. More preferred oxygen to platinum group metal weight ratios are from 5,000:1 to 35,000:1.

The fuel additive compositions can contain other additives such as detergents, antioxidants and octane improvers which are known as beneficial, but the use of such is not an essential feature of the invention.

The following examples are presented for the purpose of further illustrating and explaining the present invention and the best mode for carrying it out, and are not to be taken as limiting.

EXAMPLE 1

Dibenzyl cyclooctadiene Pt II was used as a catalyst in unleaded gasoline supplied to an automobile engine.

Production of dibenzyl cyclooctadiene platinum II was accomplished by slurrying 24.0 grams (0.064 mole) cyclooctadienyl Pt II dichloride in 200 milliliters of xylene. To the resultant mixture was added 0.5 mole benzyl magnesium chloride in diethyl ether (300 milliliters). The Grignard reaction was continued overnight, followed by hydrolysis with saturated ammonium sulfate solution in an ice bath. Following hydrolysis, the mixture was shaken vigorously and the layers were then allowed to separate. The organic phase was collected, dried over anhydrous sodium sulfate, and the residual diethyl ether was removed, leaving a solution of the product in xylene. This product has the structure:

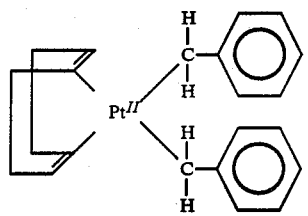

The xylene solution of the platinum compound (0.17% by weight platinum) was admixed with other fuel additive components set forth in Table 1A below.

A series of dynamometer tests were conducted, in which a 1984 Buick V-6 spark ignition engine was connected to and loaded by an eddy current dynamometer. The engine had the following specifications:

| Engine Type | Buick 90° V-6 |
| --- | --- |
| Bore and Stroke | 3.800 × 3.400 |
| Piston Displacement | 231 cu. in. |
| Compression Ratio | 8.0:1 |
| Carburetor Type | 2 BBL-ROCH |
| Air - Fuel/Ratio | 14.7:1 |

Data gathered during comparative engine tests run on the Buick V-6 engine using unleaded Indolene gasoline with a platinum-based fuel additive formulation based on the following ingredients with a fuel employing all components of the formulation except the platinum compound:

TABLE 1A

|  | Percent by Weight |
| --- | --- |
| Xylene | 58.6 |
| Methyl Tertiary Butyl Ether | 40.5 |
| Detergent (Ethyl MPA-448) | 0.9 |
| Platinum Coordination Compound as prepared above | 0.012 |
| This platinum compound has the following elemental breakdown: | |
| Platinum | 40.2% |
| Carbon | 54.4% |
| Hydrogen | 5.4% |

The engine was run under steady conditions for about ninety (90) minutes per run at about 1300 rpm and was loaded to about 79 ft. lb. torque by a dynamometer to develop, on an average, 19.6 horsepower throughout each run.

During each of these runs, the time the engine took to consume a measured 900-milliliter quantity of gasoline with and without the platinum compound was recorded. For each run, such time readings were taken on three occasions and the time averaged. The product of the horsepower and average time (in minutes) to use 900 milliliters of fuel gave numbers representing work. The results are summarized below in Table 1B.

TABLE 1B

| Baseline Run | Work | Run with Additive | Work |
| --- | --- | --- | --- |
| 1 | 176.4 | 1 | 186.2 |
| 2 | 178.3 | 2 | 182.7 |
| 3 | 176.1 | 3 | 184.1 |
| 4 | 175.8 | 4 | 181.5 |
| 5 | 179.2 | 5 | 184.0 |
| 6 | 178.8 | 6 | 189.5 |
| 7 | 180.0 | 7 | 184.3 |
| 8 | 177.1 | 8 | 183.0 |

TABLE 1B-continued

| Baseline Run | Work | Run with Additive | Work |
|---|---|---|---|
| 9 | 180.5 | 9 | 183.3 |
| 10 | 178.8 | 10 | 182.4 |
| 11 | 179.7 | 11 | 183.5 |
| 12 | 182.7 | | |
| 13 | 181.8 | | |

The consumption times for 900 milliliters of gasoline containing 0.1 ppm of platinum supplied by the platinum compound were generally longer than the consumption times without the platinum compound. The average time with the platinum compound was 9.39 minutes, and without was 9.11 minutes. This improvement of fuel consumption due to the platinum compound was 3.1%. Fuel flow measurements showed a range of fuel efficiency gains of three percent (3%) to six percent (6%) with the platinum-based additive compared to the fuel additive formulation minus the platinum-based compound in a series of similar tests.

EXAMPLE 2

The procedure of Example 1 was repeated, but this time employing 5% ethanol in addition to the fuel additive of Example 1 (at 0.2 ppm of platinum w/v). Baseline data was collected for 2 days and test data was noted on 12 days after an initial five days of operation employing the additive. The test engine was run at three rpm's (1300, 1800 and 2100) in sequence on each test day, all at a torque of 55 lb. ft. The data collected for fuel flow and hydrocarbon and carbon monoxide emissions are summarized below in Table 2.

TABLE 2

| RPM | Fuel Flow (ml/sec) | | Hydrocarbons (ppm w/v) | | Carbon Monoxide (%) | |
|---|---|---|---|---|---|---|
| | Baseline | With Additive | Baseline | With Additive | Baseline | With Additive |
| 1300 | 1.12 | 1.07 | 210 | 135 | 1.79 | 0.62 |
| 1800 | 1.82 | 1.76 | 169 | 113 | 1.05 | 0.40 |
| 2100 | 2.20 | 2.15 | 120 | 73 | 0.53 | 0.17 |

EXAMPLE 3

Additive testing was performed with a Buick engine having the specifications described in Example 1, mounted on a Superflow SF-901 water brake dynamometer. Superflow data collection capabilities included automatic measuring and recording of rpm torque, horsepower, as well as various temperatures, pressures, and flow rates.

Two of the engines spark plugs were fitted with Kistler spark plug pressure adapters (Model 640) and Kistler high impedance pressure transducers (Model 6001). An A.V.L. optical shaft encoder was mounted on the test engine which generated signals for bottom dead center and every half degree of crank angle.

Pressure and crank angle data were collected, stored and processed by a Columbia computer (Model 4220). Individual samples consisted of two pressure measurements for every half degree of shaft rotation over eighty firing cycles.

Each additive set forth in Table 3 below was tested in the following manner. A baseline test was performed without fuel treatment, followed by a test in which additive was present in the fuel, and finally the baseline test was repeated. Two pressure samples were collected during each test run. Tests were twelve and one half minutes in duration, with 20 minutes run time between tests to allow for conditioning or purging. The test engine was run at 2100 rpm and 55 lb. ft. of torque. Superflow data collection was sampled at ten second intervals. Standard deviation of horsepower was produced after each test in order to confirm engine stability and repeatability. Typical standard deviations averaged 0.06, for twelve and one-half minutes of test engine run time.

The base fuel in each of the formulations tested was AMOCO unleaded regular gasoline having an octane rating of 87. In each case where ethanol (ETOH) or tetrahydrofuron (THF) was employed, its concentration was 0.25%. The dibenzyl Pt(II) referred to in the table was dibenzyl cyclooctadiene platinum II as prepared in Example 1; and, the nitrobenzyl Pt(II) was similarly prepared by nitrating the two benzyl groups shown in the formula set forth in Example 1. Each of these platinum compounds, when employed, was used at a level sufficient to provide 0.15 ppm platinum, except where noted as being otherwise, e.g., $c=0.1$, $c=0.2$, or $c=0.3$ ppm. (The notation (all) indicates that this table summarizes data at all ethanol levels.)

For each test run which consisted of a baseline-additive-baseline sequence, the pressure measurements were plotted automatically as described above.

For each plot obtained, three parameters were studied:

1. Peak—The maximum pressure achieved in the cylinder during combustion.
2. Distance—A physical measurement of the horizontal distance between the top dead center axis and the peak of the pressure curve. Shorter distances between top dead center and peak pressure achieved indicate faster propagation of the flame front across the cylinder.
3. MIP—The mean indicated pressure is the average pressure achieved after ignition at top dead center and is an indication of the total work release achieved by combusting the fuel.

In evaluating pressure curves with additive increases in peak pressure and MIP and decreases (shorter) distances were interpreted as a beneficial effect produced by the additive in terms of fuel utilization and useful work derived from combusting the fuel.

The nature of the effect of an additive treatment to fuel was studied by using the Analysis of Variance model otherwise known as (ANOVA). The assumptions that were made for this model have the following features:

1. There are two factor levels under study; baseline and treated conditions.
2. For each factor, the probability distribution of the data is normal.
3. All probability distributions of the factors have constant variance.
4. The mean for the data at each factor level may differ, reflecting the various effects of the treatment.

A statistical test can be performed to determine whether the means of the two factors are equal. If they are not, then further analysis is required. This analysis involves the construction of an interval estimation of the mean response for a given factor, and comparison of mean responses for different factors. Statistical inferences can be made by using the interval estimation, i.e., it can be estimated with 80 or 90 percent confidence that the mean increase of the peak, distance or MIP are between the lower limit and the upper limit of the interval constructed. The interval estimation depends on the confidence level, the total number of points in the data as well as the variance of the difference of the two means. Thus conclusion can be made about the effect of the fuel treatment compared to nontreatment.

TABLE 3

| Confidence Level | | Lower Limit | Upper Limit |
|---|---|---|---|
| ETOH vs BLANK | | | |
| 80% | Peak | 0.75% | 2.40% |
| | Dist | −0.39% | 0.03% |
| | MIP | −0.43% | 0.17% |
| 90% | Peak | 0.42% | 2.72% |
| | Dist | −0.47% | 0.12% |
| | MIP | −0.55% | 0.29% |
| DIBENZYL PT(II) vs BLANK | | | |
| 80% | Peak | −0.11% | 1.05% |
| | Dist | 0.10% | 0.58% |
| | MIP | −1.23% | 0.64% |
| 90% | Peak | −0.34% | 1.27% |
| | Dist | 0.01% | 0.67% |
| | MIP | −1.59% | 1.01% |
| ETOH + DIBENZYL PT(II) vs BLANK | | | |
| 80% | Peak | 3.50% | 6.34% |
| | Dist | −0.93% | 0.39% |
| | MIP | −0.22% | 0.45% |
| 90% | Peak | 2.94% | 6.89% |
| | Dist | −1.19% | 0.64% |
| | MIP | −0.35% | 0.59% |
| THF vs BLANK | | | |
| 80% | Peak | 0.13% | 1.05% |
| | Dist | −0.29% | 0.11% |
| | MIP | −1.29% | −0.69% |
| 90% | Peak | −0.05% | 1.23% |
| | Dist | −0.36% | 0.19% |
| | MIP | −1.41% | −0.57% |
| NITROBENZYL PT(II) vs BLANK | | | |
| 80% | Peak | −0.96% | 0.76% |
| | Dist | −0.39% | 0.28% |
| | MIP | −1.21% | −0.52% |
| 90% | Peak | −1.30% | 1.09% |
| | Dist | −0.53% | 0.41% |
| | MIP | −1.34% | −0.39% |
| NITROBENZYL PT(II) + THF vs BLANK | | | |
| 80% | Peak | 1.09% | 1.99% |
| | Dist | −0.83% | −0.05% |
| | MIP | −0.91% | 0.36% |
| 90% | Peak | 0.92% | 2.16% |
| | Dist | −0.98% | 0.10% |
| | MIP | −1.16% | 0.60% |
| ETOH + DIBENZYL PT(II) vs ETOH (c = 0.1) | | | |
| 80% | Peak | −3.22% | 3.69% |
| | Dist | −1.12% | 0.98% |
| | MIP | −1.15% | 1.17% |
| 90% | Peak | −5.11% | 5.59% |
| | Dist | −1.69% | 1.56% |
| | MIP | −1.78% | 1.80% |
| ETOH + DIBENZYL PT(II) vs ETOH (c = 0.2) | | | |
| 80% | Peak | −2.54% | 4.45% |
| | Dist | −1.51% | 0.53% |
| | MIP | −0.40% | 0.10% |
| 90% | Peak | −4.46% | 6.36% |
| | Dist | −2.07% | 1.09% |
| | MIP | −0.54% | 0.24% |
| ETOH + DIBENZYL PT(II) vs ETOH (c = 0.3) | | | |
| 80% | Peak | −2.49% | 4.22% |
| | Dist | −1.51% | 0.67% |
| | MIP | −0.23% | 0.62% |
| 90% | Peak | −4.33% | 6.05% |
| | Dist | −2.10% | 1.26% |
| | MIP | −0.47% | 0.86% |
| ETOH + DIBENZYL PT(II) vs ETOH (ALL) | | | |
| 80% | Peak | 0.56% | 1.81% |
| | Dist | −0.47% | −0.04% |
| | MIP | 0.12% | 0.72% |
| 90% | Peak | 0.36% | 2.01% |
| | Dist | −0.54% | 0.03% |

TABLE 3-continued

| Confidence Level | | Lower Limit | Upper Limit |
|---|---|---|---|
| | MIP | 0.03% | 0.81% |

EXAMPLE 4

Following the test procedure of Example 3, (1) osmium (III) tris (acetylacetonate) and (2) bis (cyclopentadienyl) osmium (II) were tested against the base fuel with no additive as set forth in Example 3. The effect of each compound on peak, MIP and distance compared to base fuel was evaluated with the results as set forth in Table 4:

TABLE 4

| | % Change | | |
|---|---|---|---|
| Compound Tested | Peak | MIP | Distance |
| (1) | +0.125 | −0.029 | +0.079 |
| (2) | +5.86 | +0.847 | 0 |

EXAMPLE 5

This example compares, by the procedure of Example 1, the effectiveness of a fuel additive set forth in Table 5A to that set forth in Table 1A, both being in accordance with the invention. The platinum and rhodium coordination compounds noted in the table were prepared as in Example 1 and added as xylene solutions having a metal content of 0.5%.

TABLE 5A

| Ingredient | Parts by Weight |
|---|---|
| Methyl tertiary butyl ether | 39 |
| Ethanol | 30 |
| Exxon LOPS mineral spirits | 20 |
| Xylene | 9 |
| MPA-448 gasoline detergent | 1.5 |
| Platinum coordination compound solution | 0.4 |
| Rhodium coordination compound solution | 0.06 |
| (Atomic ratio of Pt:Rh = 80:20) | |

The time to consume 900 ml of fuel was measured at the various rpm's and torques noted with the results shown in Table 5B, below.

TABLE 5B

| rpm | Torque (ft.lb) | Average Fuel Flow (min:sec) | Hydrocarbon Average (ppm) | Average CO (%) |
|---|---|---|---|---|
| Baseline (Table 1A) | | | | |
| 2100 | 55 | 6:59.43 | 78 | .22 |
| 1800 | 48.8 | 8:33.91 | 109 | .57 |
| 1300 | 32.6 | 13:36.73 | 146 | 1.04 |
| Treated (Table 5A) | | | | |
| 2100 | 55 | 7:15.87 | 43 | .24 |
| 1800 | 48.8 | 8:56.71 | 61 | .45 |
| 1300 | 32.6 | 14:31.89 | 85 | .58 |

The above description is for the purpose of teaching the person of ordinary skill in the art how to practice the present invention and is not intended to detail all those obvious modifications and variations of it which will become apparent to the skilled worker upon reading the description. It is intended, however, that all such obvious modifications and variations be included within the scope of the present invention which is defined by the following claims.

We claim:

1. A method of reducing emissions from or increasing the utilizable energy of gasoline for powering internal combustion engines, comprising admixing with gasoline a fuel soluble organo-metallic fuel additive composition in an amount effective to supply from 0.01 to 1.0 parts per million of platinum per part of fuel, said composition comprising a compound having the general formula $$XPtR_1R_2$$

wherein X is a ligand containing at least one unsaturated carbon-to-carbon bond with an olefinic, acetylenic or aromatic pi bond configuration and $R_1$ and $R_2$ are, independently, benzyl, phenyl, nitrobenzyl or alkyl having from 1-10 carbons.

2. The method of claim 1 wherein X is a dipyridyl or cyclooctadienyl ligand.

3. The method of claim 1 wherein $R_1$ and $R_2$ are both methyl, phenyl or benzyl.

4. The method of claim 1 wherein said fuel additive composition further comprises a fuel-soluble solvent for said platinum compound.

5. The method of claim 4 wherein said platinum and said solvent are present in amounts sufficient to supply oxygen and metal at a weight ratio of from 1,000:1 to 100,000:1.

6. The method of claim 5 wherein said solvent is an alcohol having from one to four carbon atoms and is employed at a level of from 0.25 to about 5 percent by weight of the fuel.

7. The method of claim 4 wherein said alcohol is ethanol employed at a level up to about 1 percent of said composition and sad platinum is present at a level of from 0.05 to 0.5 parts per million parts fuel.

8. The method of claim 4 wherein said solvent comprises ethanol, tetrahydrofuran, methyl tertiary butyl ether, or combinations of these.

9. The method of claim 8 wherein $R_1$ and $R_2$ each comprise benzyl and said solvent comprises ethanol.

10. The method of claim 8 wherein $R_1$ and $R_2$ each comprise nitrobenzyl and said solvent comprises tetrahydrofuran.

11. The method of claim 8 wherein said solvent comprises methyl tertiary butyl ether.

12. A method of increasing the utilizable energy of gasoline for powering internal combustion engines, comprising admixing with gasoline a fuel soluble organo-metallic fuel additive composition in an amount effective to supply from 0.01 to 1.0 parts per million of platinum group metal per part of fuel, said composition comprising compounds selected from the group consisting of 2,2'-bis (N, N-dialkylamino) 1,1'-diphenyl metals of the general formula

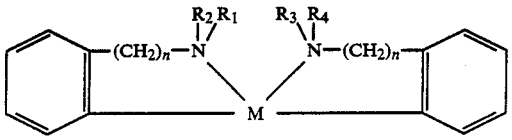

wherein M is platinum, palladium, rhodium or iridium; $R_1$–$R_4$ are, independently, alkyl having from 1–10 carbons; and n is an integer from 1–5; tetrakis (alkoxy carbonyl) metal cycloalkenes of the general formula $$R_2MC_4(COOR_1)_4$$

wherein M is a platinum, palladium, rhodium or iridium; $R_1$ is alkyl having from 1–5 carbons; and $R_2$ is cycloalkene having from 5–8 carbons and from 2–4 unsaturations in the ring structure; bis(cyclopentadiene) acetylene dipalladium compounds of the general formula $$(\phi C\ C\phi)\ (C_5\phi_5)_2Pd_2$$

wherein $\phi$ is phenyl; dialkyl dipyridyl metals of the formula $$R_1R_2M(C_{10}H_8N_2)$$

wherein $R_1$ and $R_2$ are alkyl having from 1–10 carbons; and M is platinum, palladium, rhodium or iridium; and bis ($\pi$-allyl) metals of the general formula $$(R-C_3H_4)_2M$$

wherein M is platinum, palladium, iridium and rhodium; and R is hydrogen, aryl or alkyl having from 1–10 carbons.

13. The method of claim 12 wherein said compound is selected from the group consisting of 2,2'-bis (N,N-dimethylamino) 1,1'-diphenyl palladium; tetrakis (methoxy carbonyl) palladia cyclopentadiene; $\mu$-diphenyl acetylene bis ($\eta^5$-pentaphenyl cyclopentadiene) dipalladium; and bis (phenyl allyl) palladium.

14. The method of claim 12 wherein said fuel additive composition further comprises a fuel-soluble solvent for said metal compound.

15. The method of claim 14 wherein said metal and said solvent are present in amounts sufficient to supply oxygen and metal at a weight ratio of from 1,000:1 to 100,000:1.

16. The method of claim 15 wherein said solvent is an alcohol having from one to four carbon atoms and is employed at a level of from 0.25 to about 5 percent of the weight of the fuel.

17. The method of claim 16 wherein said alcohol is ethanol employed at a level up to about 1 percent of said composition and said metal is present at a level of from 0.05 to 0.5 parts per million parts fuel.

18. The method of claim 14 wherein said solvent comprises ethanol, tetrahydrofuran, methyl tertiary butyl ether, or combinations of these.

* * * * *